US011446317B2

(12) United States Patent
Ikenaga et al.

(10) Patent No.: US 11,446,317 B2
(45) Date of Patent: Sep. 20, 2022

(54) INOSITOL PHOSPHATE-CONTAINING COMPOSITION

(71) Applicant: OTSUKA PHARMACEUTICAL CO., LTD., Tokyo (JP)

(72) Inventors: Takeshi Ikenaga, Osaka (JP); Hiroki Noguchi, Osaka (JP); Chieko Kohashi, Osaka (JP); Noriyuki Kouda, Osaka (JP); Ayako Takaishi, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/759,162

(22) PCT Filed: Oct. 26, 2017

(86) PCT No.: PCT/JP2017/038720
§ 371 (c)(1),
(2) Date: Apr. 24, 2020

(87) PCT Pub. No.: WO2019/082335
PCT Pub. Date: May 2, 2019

(65) Prior Publication Data
US 2021/0177876 A1 Jun. 17, 2021

(51) Int. Cl.
*A61K 31/7028* (2006.01)
*A61P 43/00* (2006.01)
*A61P 1/16* (2006.01)
*A61P 3/10* (2006.01)
*A61P 9/12* (2006.01)
*A61P 13/02* (2006.01)
*A61K 31/19* (2006.01)

(52) U.S. Cl.
CPC .......... *A61K 31/7028* (2013.01); *A61K 31/19* (2013.01); *A61P 1/16* (2018.01); *A61P 3/10* (2018.01); *A61P 9/12* (2018.01); *A61P 13/02* (2018.01); *A61P 43/00* (2018.01)

(58) Field of Classification Search
None
See application file for complete search history.

(56) References Cited

U.S. PATENT DOCUMENTS

| 4,952,568 A | 8/1990 | Sawai et al. |
| 5,023,248 A | 6/1991 | Siren |

FOREIGN PATENT DOCUMENTS

| CN | 102379385 A | 3/2012 |
| CN | 106070659 A | 11/2016 |
| EP | 0 349 143 A2 | 1/1990 |
| EP | 1306431 A1 | 5/2003 |
| JP | H01-294631 A | 11/1989 |
| JP | H02-15032 A | 1/1990 |
| JP | H04-270296 A | 9/1992 |
| JP | H07-228540 A | 8/1995 |
| JP | 2006-342128 A | 12/2006 |
| JP | 2007-236201 A | 9/2007 |
| JP | 2008-94837 A | 4/2008 |
| JP | 2009-149530 A | 7/2009 |
| JP | 2014-532758 A | 12/2014 |
| JP | 2017-39762 A | 2/2017 |
| WO | 2010/092941 A1 | 8/2010 |
| WO | 2013/066349 A1 | 5/2013 |
| WO | WO-2013066352 A1 * | 5/2013 ................ A61P 7/00 |

OTHER PUBLICATIONS

Foster, Int. J. Exp. Path. (2016), 97, 397-407. (Year: 2016).*
Pittman, Am Fam Physician. Apr. 1, 1999,59(7): 1799-1806. (Year: 1999).*
Hirano, JP 11253134 A, Sep. 21, 1999, English abstract only. (Year: 1999).*
JP11253134A, 1999, machine translation (Year: 1999).*
Kolassa et al., "Adenosine uptake by the isolated epithelium of guinea pig jejunum", Can. J. Physiol. Pharmacol., vol. 55, 1977, pp. 1033-1038 (6 pages total).
Salati et al., "Absorption and Metabolism of Adenine, Adenosine-5'-Monophosphate, Adenosine and Hypoxanthine by the Isolated Vascularly Perfused Rat Small Intestine", J. Nutr., vol. 114, pp. 753-760, 1984 (8 pages total).
Harms et al., "Transport of purine nucleotides and nucleosides by in vitro rabbit ileum", Am. J. Physiol, 1977, vol. 233, No. 1, pp. E47-E55 (9 pages total).
Muraoka et al., "Inhibition of xanthine oxidase by phytic acid and its antioxidative action", Life Sciences, vol. 74, 2004, pp. 1691-1700 (10 pages total).
Grases et al., "Absorption and excretion of orally administered inositol hexaphosphate ($IP_6$ or phytate) in humans", BioFactors, vol. 15 (2001) pp. 53-61 (9 pages total).
Briviba et al., "Dephosphorylation of myo-inositol phosphates in the in vitro intestinal Caco-2 cell model", International Journal of Food Sciences and Nutrition, vol. 30, 2017, pp. 1-6 (7 pages total).
Onyango et al., "Phytic acid increases mucin and endogenous amino acid losses from the gastrointestinal tract of chickens", British Journal of Nutrition (2009), vol. 101, pp. 836-842 (7 pages total).
Hayakawa et al., "Effect of Phytate on the Hydrolysis of p-Nitrophenyl Phosphate with Phosphatase from Various Sources", Agric. Biol Chem., vol. 55 No. 3, pp. 651-657, 1991 (7 pages total).
International Search Report dated Dec. 19, 2017 issued by the International Searching Authority in International Application No. PCT/JP2017/038720.

(Continued)

*Primary Examiner* — Layla D Berry
(74) *Attorney, Agent, or Firm* — Sughrue Mion, PLLC

(57) ABSTRACT

The present invention further provides a composition for inhibiting purine body absorption, a composition for inhibiting purine nucleotide metabolism, a composition for inhibiting phosphatase, a composition for inhibiting uric acid level elevation, a composition for improving blood pressure, a composition for improving blood glucose level, a composition for improving liver function, a composition for controlling serum iron level, or a composition for promoting calcium absorption, comprising an inositol phosphate or a salt thereof. The present invention further provides a composition comprising an inositol phosphate or a salt thereof, wherein the taste thereof is improved by adding thereto a predetermined amount of calcium lactate.

4 Claims, 14 Drawing Sheets

(56) References Cited

OTHER PUBLICATIONS

International Preliminary Report on Patentability with the translation of Written Opinion dated Apr. 28, 2020 issued by the International Bureau in International Application No. PCT/JP2017/038720.
Extended European Search Report dated Jun. 1, 2021 in European Application No. 17929881.5.
Leif Hallberg et al., "Phytates and the inhibitory effect of bran on iron absorption in man", American Journal of Clinical Nutrition, 1987, vol. 45, No. 5, pp. 988-996 (9 pages).

* cited by examiner

Mean ± Standard error
Control beverage vs. Phytic acid beverage: *$P<0.05$

Mean ± Standard error
Control beverage vs. Phytic acid beverage: *$P<0.05$

Mean ± Standard error

Control beverage vs. Phytic acid beverage: #$P<0.10$

Mean ± Standard error

Compared to 0 week: *$P<0.05$

Mean ± Standard error
Compared to 0 week: *$P<0.05$

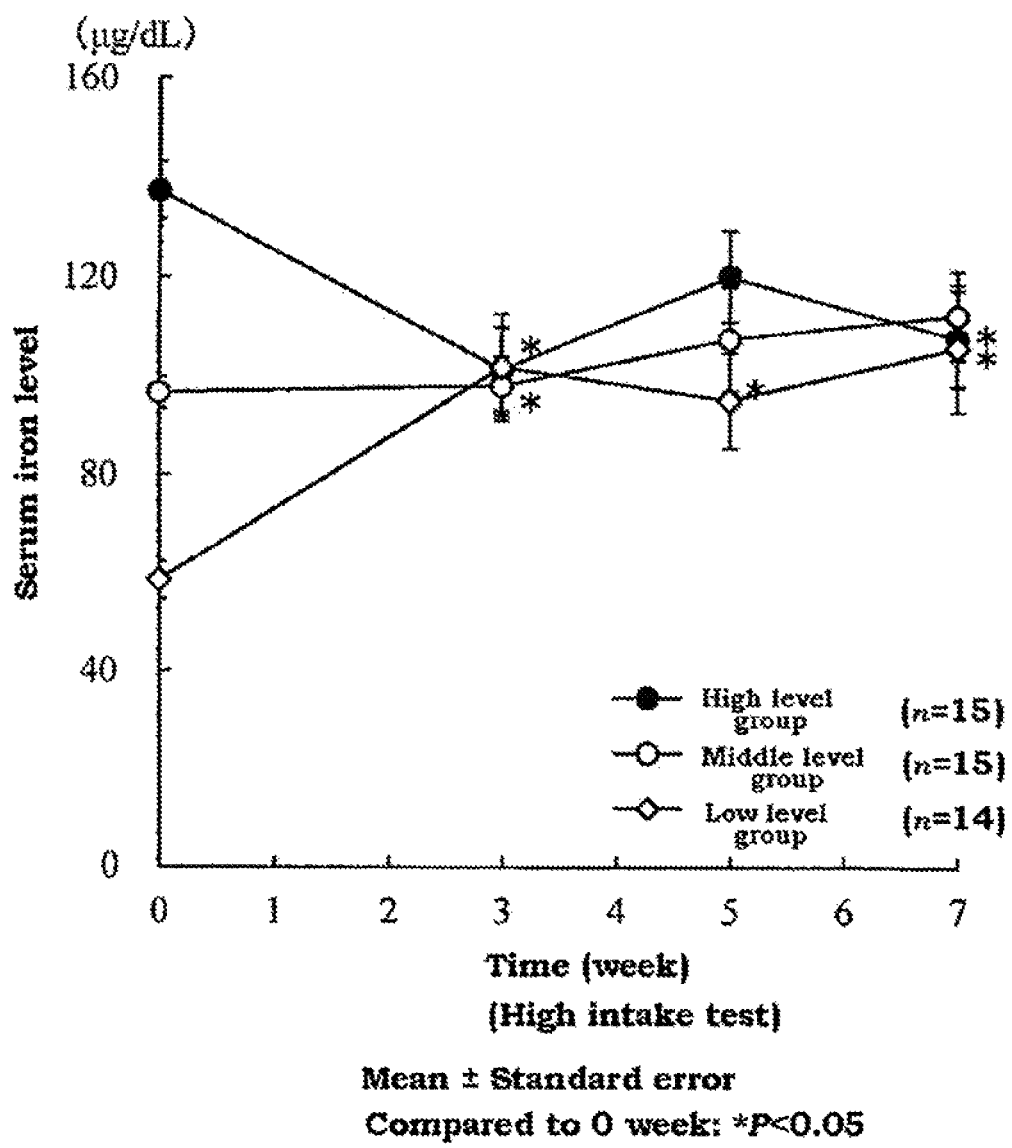

INOSITOL PHOSPHATE-CONTAINING COMPOSITION

CROSS REFERENCE TO RELATED APPLICATIONS

This application is a National Stage of International Application No. PCT/JP2017/038720 filed Oct. 26, 2017.

TECHNICAL FIELD

The present application relates to a composition for inhibiting purine body absorption, inhibiting purine nucleotide metabolism, inhibiting phosphatase, inhibiting uric acid level elevation, improving blood pressure, improving blood glucose level, improving liver function, controlling serum iron level, or promoting calcium absorption, comprising an inositol phosphate or a salt thereof. The present invention further relates to a composition having improved taste, comprising an inositol phosphate or a salt thereof.

BACKGROUND ART

The number of gout patients and hyperuricemia patients is increasing along with changes in diet, such as increased calories, protein, and fat in the diet. There is growing interest in the prevention and improvement of gout and its risk factor, hyperuricemia.

Normally, in good health, serum uric acid levels are maintained by a balance between the production and excretion of uric acid. However, if the balance between uric acid production and excretion is disturbed by excessive production, decreased excretion, or both, serum uric acid level increases, resulting in hyperuricemia (Serum urate>7.0 mg/dL in both men and women). Hyperuricemia is known to cause various diseases such as gout, arteriosclerosis, and renal impairment. Hyperuricemia is prevented and treated by controlling serum uric acid levels by reducing the intake of purine body, the source of uric acid, through diet therapy and alcohol restriction in addition to medication.

However, it is not easy to continue the purine intake restriction and the drinking restriction in the daily life, and there is a demand for the development of an effective medicine and/or food capable of easily reducing the internal absorption of dietary purines. There is also a strong need for health foods that can maintain/improve blood pressure, blood glucose level, liver function, iron level, bone health, etc., according to the increasing health consciousness.

A purine body is a generic term for compounds having a common structure called a purine skeleton, and plays various functions in vivo, such as transmitting genetic information as a constituent of nucleic acids. Purine body includes purine base (e.g. adenine, guanine, hypoxanthine), purine nucleoside, which is a purine base linked to a sugar, (e.g. adenosine, guanosine, and inosine), and purine nucleotide, which is a purine nucleoside linked to phosphate group(s), (e.g. adenylic acid (AMP), guanylic acid (GMP), inosinic acid (IMP)).

Purine bodies are delivered in vivo as dietary purine bodies from food via intestinal absorption and are also biosynthesized by de novo or salvage pathways. In human, purine bodies are ultimately metabolized to uric acid.

Most of the purine bodies contained in foods are present as components of nucleic acids (nucleotide residues). Normally, nucleic acids are broken down into nucleotides by nucleases or phosphodiesterases in the intestine, nucleotides are broken down into nucleosides by alkaline phosphatase or 5'-nucleotidase, and nucleosides are further broken down into bases and sugars.

It has been suggested that purine bodies of the intestinal absorption are purine nucleosides and purine bases, whereas purine nucleotides and nucleic acids cannot pass through the intestinal tract (Non-Patent Documents 1, 2, and 3).

For metabolism of purine bodies to uric acid:

for example,

AMP is converted to adenosine by 5'-nucleotidase activity, and adenosine is metabolized via inosine to hypoxanthine. Hypoxanthine is converted to xanthine by xanthine oxidase activity;

GMP is converted to guanosine by 5'-nucleotidase activity, and guanosine is converted to xanthine via guanine;

IMP is converted to inosine by 5'-nucleotidase activity, followed by hypoxanthine to xanthine similar to AMP; and Xanthine is converted to uric acid by xanthine oxidase activity, and uric acid is excreted by the kidneys and intestine.

Drugs for treatment of hyperuricemia are mainly divided into a uric acid production inhibitor and a uric acid excretion promoter, and for example, a xanthine oxidase inhibitor (for example, allopurinol) is used as the uric acid production inhibitor.

Phytic acid (inositol hexaphosphate) is abundant in rice bran, germ, corn, beans etc. and has been ingested for many years. Phytic acid is known to have a chelating action and an antioxidant action, as well as a blood coagulation preventing action, a hypercalciuria preventing action and a lipid improving action.

Non-Patent Document 4 discloses that phytic acid inhibits xanthine oxidase activity to inhibit conversion of xanthine to uric acid, the $IC_{50}$ of which, however, is about 30 mM (19.8 g/L), and the concentration is very high.

Patent Document 1 merely recites phytic acid as an example of a xanthine oxidase inhibitor, which is a uric acid-lowering drug, but there is no specific description of the effect of phytic acid.

PRIOR ART DOCUMENT

Patent Document

Patent Document 1: JP 2017-39762 A

Non-Patent Document

Non-Patent Document 1: Kolassa N, Stengg R, Turnheim K 1977 Adenosine uptake by the isolated epithelium and guinea pig jejunum. Can J Physiol Pharmacol 55:1033-1038

Non-Patent Document 2: Salati L M, Gross C J, Henderson L M, Savaiano D A 1984 Absorption and metabolism of adenine, adenosine-5'-mono-phosphate, adenosine and hypoxanthine by the isolated vascularly perfused rat small intestine. J Nutr 114:753-760

Non-Patent Document 3: Harms V, Stirling C E: Transport of purine nucleotides and nucleosides by in vitro rabbit ileum. Am J Physiol 1977; 233: E47-E55

Non-Patent Document 4: Muraoka, S., Miura, T., 2004. Inhibition of xanthine oxidase by phytic acid and its antioxidative action. Life Sciences 74, 1691-1700.

Non-Patent Document 5: Grases F. et al. BioFactors 2001; 15:53.61

Non-Patent Document 6: Briviba K et al., Int J Food Sci Nutr. 2017; 30:1-6

The disclosures of the prior art documents cited herein are hereby incorporated by reference in their entirety.

SUMMARY

Technical Problem

It is an object of the present invention to provide a composition for inhibiting the absorption of purine bodies contained in daily meals through the intestinal tract, which has excellent effects, is excellent in safety, and can be continuously taken as a health food, supplement, etc. Furthermore, it is an object of the present invention to provide a safe and effective composition which can improve blood pressure, blood glucose level, liver function, serum iron level, or calcium absorption and can be taken in daily and continuously. Further, it is preferable that the composition has little bitterness and harsh taste to be continuously ingested. It is also an object of the present invention to provide a method for improving the taste of the composition.

Solution to Problem

The inventors of the present invention have been intensively studied to solve the above problems, and have found that an inositol phosphate inhibits metabolism of purine nucleotides to purine nucleosides to suppress absorption of dietary purine bodies through the intestinal tract and has an improving action on blood pressure, blood glucose level, liver function, serum iron level, and calcium absorption, thereby reaching the present invention. Furthermore, although an inositol phosphate (especially phytic acid) has a unique bitterness and harsh taste, the inventors have found that a combination with calcium lactate improves the taste.

The present invention provides:

[1] A composition for inhibiting purine body absorption, comprising an inositol phosphate or a salt thereof.
[2] The composition according to [1], wherein the purine body absorption is purine body absorption through an intestinal tract.
[3] A composition for inhibiting purine nucleotide metabolism, comprising an inositol phosphate or a salt thereof.
[4] The composition according to [3], wherein the purine nucleotide metabolism is metabolism from purine nucleotide to purine nucleoside.
[5] A composition for inhibiting phosphatase, comprising an inositol phosphate or a salt thereof.
[6] A composition according to [5], wherein the phosphatase is alkaline phosphatase and/or 5'nucleotidase.
[7] The composition according to any one of [1] to [6], comprising 0.1 wt % to 90 wt % of the inositol phosphate or a salt thereof as the inositol phosphate.
[8] The composition according to any one of [1] to [7], wherein a dose of the inositol phosphate or a salt thereof per administration is 10 mg to 15 g as the inositol phosphate.
[9] The composition according to any one of [1] to [8], wherein a dose of the inositol phosphate or a salt thereof per day is 10 mg to 15 g as the inositol phosphate.
[10] The composition according to any one of [1] to [9], wherein the inositol phosphate or a salt thereof is phytic acid or a salt thereof.
[11] The composition any one of [1] to [10],
wherein
said composition further comprises calcium lactate in a weight ratio of inositol phosphate:calcium lactate=1:0.2 to 1:0.5, and
said composition is liquid.
[12] A composition for inhibiting uric acid level elevation, comprising an inositol phosphate or a salt thereof, wherein a dose of the inositol phosphate or a salt thereof per administration is 10 mg to 15 g as the inositol phosphate.
[13] The composition for inhibiting uric acid level elevation according to [12], wherein said composition inhibits purine body absorption through an intestinal tract.
[14] The composition according to [12] or [13], comprising 0.1 wt % to 90 wt % of the inositol phosphate or a salt thereof as the inositol phosphate.
[15] The composition according to any 1 of [12] to [14], wherein a dose of the inositol phosphate or a salt thereof per day is 10 mg to 15 g as the inositol phosphate.
[16] The composition according to any one of [12] to [15], wherein the inositol phosphate or a salt thereof is phytic acid or a salt thereof.
[17] The composition any one of [12] to [16],
wherein
said composition further comprises calcium lactate in a weight ratio of inositol phosphate:calcium lactate=1:0.2 to 1:0.5, and
said composition is liquid.
[18] A composition for improving blood pressure, comprising an inositol phosphate or a salt thereof.
[19] A composition for improving blood glucose level, comprising an inositol phosphate or a salt thereof.
[20] A composition for improving liver function, comprising an inositol phosphate or a salt thereof.
[21] A composition for controlling serum iron level, comprising an inositol phosphate or a salt thereof.
[22] A composition for promoting calcium absorption, comprising an inositol phosphate or a salt thereof.
[23] The composition according to any one of [18] to [22], comprising 0.1 wt % to 90 wt % of the inositol phosphate or a salt thereof as the inositol phosphate.
[24] The composition according to any one of [18] to [23], wherein a dose of the inositol phosphate or a salt thereof per administration is 10 mg to 15 g as the inositol phosphate.
[25] The composition according to any one of [18] to [24], wherein a dose of the inositol phosphate or a salt thereof per day is 10 mg to 15 g as the inositol phosphate.
[26] The composition according to any one of [18] to [25], wherein the inositol phosphate or a salt thereof is phytic acid or a salt thereof.
[27] The composition any one of [18] to [26],
wherein
said composition further comprises calcium lactate in a weight ratio of inositol phosphate:calcium lactate=1:0.2 to 1:0.5, and
said composition is liquid.
[28] A liquid composition comprising an inositol phosphate or a salt thereof and calcium lactate in a weight ratio of inositol phosphate:calcium lactate=1:0.2 to 1:0.5.

Furthermore, the present invention provides use of an inositol phosphate or a salt thereof in the manufacture of a composition for inhibiting purine body absorption, a composition for inhibiting purine nucleotide metabolism, a composition for inhibiting phosphatase, a composition for inhibiting uric acid level elevation, a composition for improving blood pressure, a composition for improving blood glucose level, a composition for improving liver function, a composition for controlling serum iron level, or a composition for promoting calcium absorption.

The present invention further provides a method for inhibiting purine body absorption, a method for inhibiting purine nucleotide metabolism, a method for inhibiting phosphatase, a method for inhibiting uric acid level elevation, a method for improving blood pressure, a method for improving blood glucose level, a method for improving liver function, a method for controlling serum iron level, or a composition for promoting calcium absorption, comprising administering an inositol phosphate or a salt thereof.

In addition, the present invention provides an inositol phosphate or a salt thereof for use in inhibiting purine body absorption, inhibiting purine nucleotide metabolism, inhibiting phosphatase, inhibiting uric acid level elevation, improving blood pressure, improving blood glucose level, improving liver function, controlling serum iron level, or promoting calcium absorption.

Effect of Invention

An inositol phosphate is a substance having abundant dietary experience and high safety and is readily available, and the present invention provides a composition for inhibiting purine body absorption, a composition for inhibiting purine nucleotide metabolism, a composition for inhibiting phosphatase, a composition for inhibiting uric acid level elevation, a composition for improving blood pressure, a composition for improving blood glucose level, a composition for improving liver function, a composition for controlling serum iron level, or a composition for promoting calcium absorption, which can be ingested continuously over a long period of time.

Further, the present invention provides an inositol phosphate-containing composition having suppressed harsh taste and bitterness, which allows the composition to be ingested more easily for a long-term and continuously.

BRIEF DESCRIPTION OF DRAWINGS

FIG. 3-1 shows the IAUC (0 to 360 minutes) of serum uric acid in humans after ingestion of a high-purine diet (FAS).

FIG. 3-2 shows the IAUC (0 to 360 minutes) of serum uric acid in humans after ingestion of a high-purine diet (PPS).

FIG. 3-3 shows the cumulative urinary uric acid excretion (0 to 360 minutes) in humans after ingestion of a high-purine diet (FAS).

FIG. 3-4 shows the cumulative urinary uric acid excretion (0 to 360 minutes) in humans after ingestion of a high-purine diet (PPS).

FIG. 4-1 shows the change in the mean values of systolic blood pressure in the high intake test.

FIG. 4-2 shows the change in the mean values of diastolic blood pressure in the high intake test.

FIG. 5-1 shows the change in the mean values of blood glucose level in the low intake test.

FIG. 5-2 shows the change in the mean values of HbA1c in the low intake test.

FIG. 7-1 shows the change in the mean values of serum iron level in the high intake test.

FIG. 7-2 shows the change in the mean values of serum iron level in the low intake test.

DESCRIPTION OF EMBODIMENTS

Figure 1:
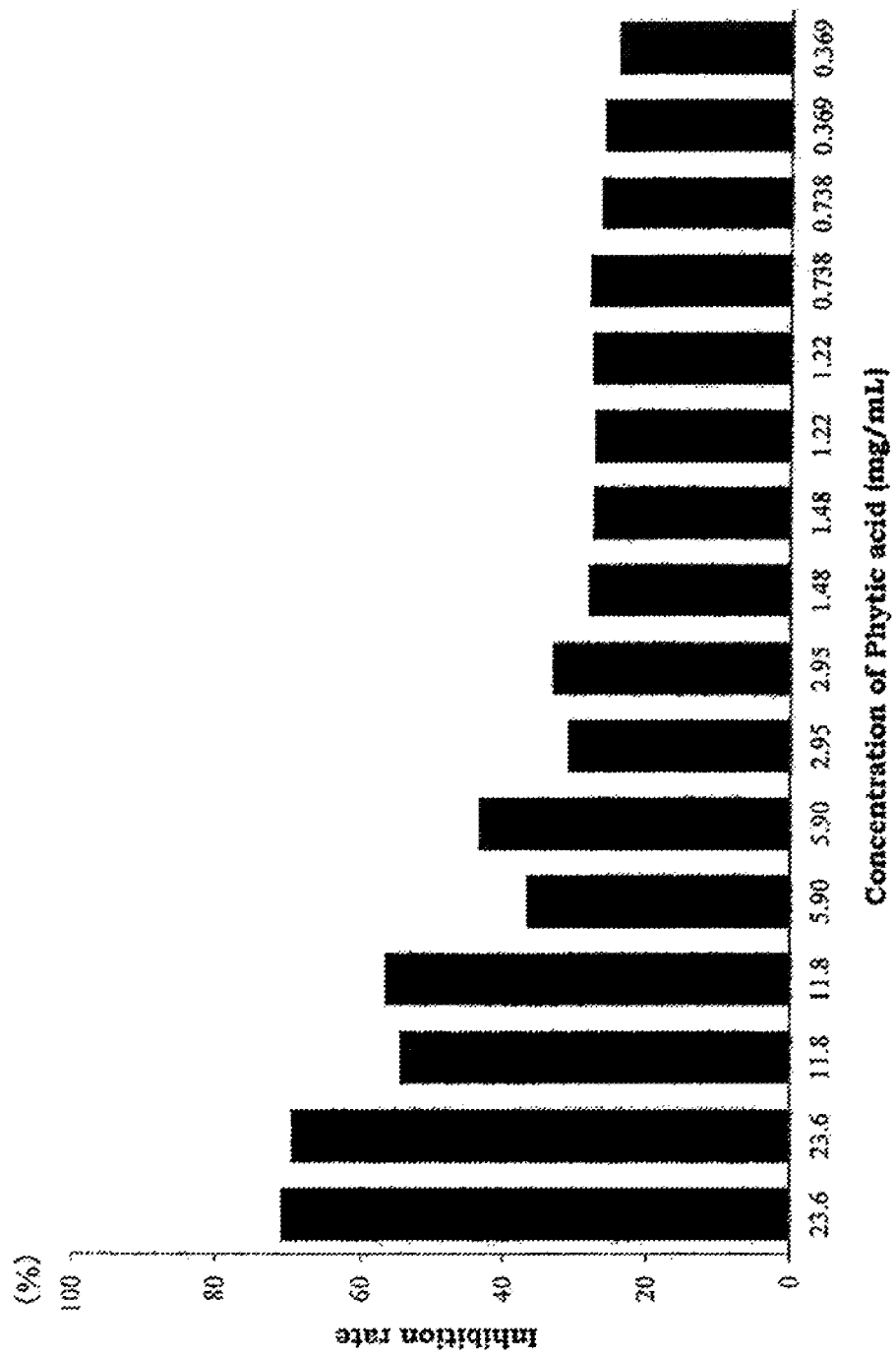
FIG. 1 shows the rate of metabolism inhibition of inosine monophosphate to inosine by various concentrations of phytic acid using rat intestinal powder.

The present invention relates to a composition for inhibiting purine body absorption, a composition for inhibiting purine nucleotide metabolism, a composition for inhibiting phosphatase, a composition for inhibiting uric acid level elevation, a composition for improving blood pressure, a composition for improving blood glucose level, a composition for improving liver function, a composition for controlling serum iron level, or a composition for promoting calcium absorption, comprising an inositol phosphate or a salt thereof.

In the present invention, an inositol phosphate means an inositol phosphate ester in which 1 to 6 hydroxy groups of the 6 hydroxy groups of inositol are phosphorylated. There are nine structural isomers of inositol, and the inositol phosphate of the present invention may have any structural isomer of inositol, but a preferred example is myo-inositol phosphate. Examples of inositol phosphate include Inositol monophosphate, Inositol 1,4-bisphosphate, Inositol 1,4,5-trisphosphate, Inositol 1,4,5,6-tetrakisphosphate, Inositol 1,3,4,5,6-pentakisphosphate, Inositol 1,2,3,4,5,6-hexakisphosphate. In the present invention, preferred examples of inositol phosphate include phytic acid, which is a hexakisphosphate of myo-inositol.

The inositol phosphate(s) can also be used in salt form. Examples of the salt(s) includes a physiologically acceptable salt, for example, alkali metal salts such as sodium salts, potassium salts, and the like; alkali earth metal salts such as calcium salts, magnesium salts, barium salts, and the like; basic amino acid salts such as arginine, lysine, and the like; ammonium salts such as ammonium salts and tricyclohexylammonium salts, and the like; various alkanolamine salts such as monoethanolamine salts, diethanolamine salts, triethanolamine salts, monoisopropanolamine salts, diisopropanolamine salts, triisopropanolamine salts, and the like. Preferred examples of salt(s) of inositol phosphate(S) of the present invention include alkali metal salts, alkaline earth metal salts, and mixtures thereof.

In the present invention, preferred examples of inositol phosphate(s) or salt(s) thereof include phytic acid, calcium phytate, sodium phytate, and mixed salts of calcium-magnesium phytate (phytin).

In the composition of the present invention, an inositol phosphate or a salt thereof may be a combination of inositol phosphate(s) and salt(s) of inositol phosphate(s). In the composition of the present invention, an inositol phosphate may be a single kind of an inositol phosphate or a combination of a plurality of kinds of inositol phosphate(s). In the composition of the present invention, a salt of an inositol phosphate may be a single kind of salt of an inositol phosphate(s) or a combination of plurality of kinds of salt(s) of inositol phosphate(s).

As an inositol phosphate or a salt thereof in the present invention, not only a high-purity product synthesized organic-chemically or by using microorganisms, but also extracts, partially purified products, or processed products of plants, microorganisms, various foods and drinks containing inositol phosphate(s) may be used. Inositol phosphate(s) or salt(s) thereof isolated from the extracts, partially purified products or processed products may also be used.

The amount of inositol phosphate(s) or salt(s) thereof contained in the composition of the present invention (food and drink, pharmaceutical composition, etc.), the amount of inositol phosphate(s) or salt(s) thereof administered per administration, and the amount of inositol phosphate(s) or salt(s) thereof administered per day are not particularly limited as long as they are within the range in which the intended effect(s) are exerted, and may be selected according to the form of the composition, the number of administrations, the health condition of the subject, etc. The administration period of the composition of the present invention is not particularly limited as long as it is within the range in which the intended effect(s) are exerted, and the composition may be administered as a single dose or continuously. In order to obtain a continuous effect of inhibiting purine body absorption, inhibiting purine nucleotide metabolism, inhibiting phosphatase, inhibiting uric acid level elevation, improving blood pressure, improving blood glucose level, improving liver function, controlling serum iron level, or promoting calcium absorption, the composition of the present invention may be desirably ingested continuously over a long period of time, for example, 2 days, 3 days, 1 week, 10 days, 1 month, or 3 months or more.

The amount of inositol phosphate(s) or salt(s) thereof comprised in the composition of the present invention may vary depending on the kind of inositol phosphate(s) or salt(s) thereof, the form of the composition, etc., and may be selected from the range of 0.1 wt % to 90 wt %, usually as the inositol phosphate(s), based on the total weight of the composition. Examples include 0.5 wt % to 90 wt %, 0.5 wt % to 85 wt %, 0.5 wt % to 80 wt %, 1 wt % to 70 wt %, and 1 wt % to 50 wt %. Additional examples of the upper limit of the amount of inositol phosphate(s) or salt(s) thereof comprised in the composition of the present application include 90 wt %, 85 wt %, 80 wt %, 70 wt %, 50 wt %, 30 wt %, 10 wt %, and 5 wt % as the inositol phosphate(s), relative to the total weight of the composition; additional examples of the lower limit of the amount of inositol phosphate(s) or salt(s) thereof comprised in the composition of the present application include 0.1 wt %, 0.5 wt %, 0.7 wt %, and 1 wt % as the inositol phosphate(s), relative to the total weight of the composition; and a preferred range of the amount of inositol phosphate(s) or salt(s) thereof comprised in the composition of the present invention may be indicated by a combination of the upper and lower limits.

When the composition of the present invention is formulated as a liquid preparation such as a beverage, the amount of inositol phosphate(s) or salt(s) thereof comprised in the composition of the present invention may be selected from the range of, for example, 0.1 to 10 wt %, preferably 0.5 wt % to 10 wt %, more preferably 0.5 wt % to 5 wt %, more preferably 1 wt % to 5 wt %, and most preferably 1 wt % to 3 wt % as the inositol phosphate(s) based on the total weight of the composition.

Further examples of the upper limit of the amount of inositol phosphate(s) or salt(s) thereof comprised in the composition of the present application when the composition is formulated as a liquid preparation such as a beverage include, as the inositol phosphate(s) relative to the total weight of the composition, preferably 10 wt %, 7 wt %, 5 wt % and 3 wt %; examples of the lower limit of the amount of inositol phosphate(s) or salt(s) thereof comprised in the composition of the present application include, as the inositol phosphate(s) relative to the total weight of the composition, preferably 0.1 wt %, 0.5 wt %, 0.7 wt %, and 1 wt %; and a preferred range of the amount of the inositol phosphate(s) or salt(s) thereof be indicated by a combination of the upper and lower limits.

It is desirable that the amount of the composition of the invention to be ingested in a single administration be in the range that can be taken for a relatively limited time (e.g. during a meal or within 30 minutes before or after a meal). When the composition of the present invention is formulated as a liquid preparation such as a beverage, examples of the ingested amount per administration include 30 to 500 mL. For the liquid preparation such as a beverage, the amount of the composition per administration may be filled in a container such as a bottle or a PET bottle. Alternatively, the amount of the composition to be ingested in multiple administrations are contained in one container, and the subject may ingest the single dose from the container at the time of administration.

When the composition of the present invention is formulated as a solid preparation such as tablets, granules, capsules, powders, chewable tablets, etc., the amount of inositol phosphate(s) or salt(s) thereof comprised in the composition of the present invention may be selected from the range of, for example, 1 to 90 wt % as the inositol phosphate(s) based on the total weight of the composition, and preferred examples thereof include 1 wt % to 90 wt %, 5 wt % to 80 wt %, 10 wt % to 70 wt %, and 50 wt % to 70 wt %. Further examples of the upper limit of the amount of inositol phosphate(s) or salt(s) thereof comprised in the composition of the present invention when the composition of the present invention is formulated as solid preparations such as tablets, granules, capsules, powders, chewable tablets, and the like, as the inositol phosphate(s) relative to the total weight of the composition, preferably include 90 wt %, 85 wt %, 80 wt %, 70 wt %, and 50 wt %; further examples of the lower limit of the amount of inositol phosphate(s) or salt(s) thereof comprised in the composition of the present application include, as the inositol phosphate(s) relative to the total weight of the composition, preferably 1 wt %, 5 wt %, 10 wt % and 20 wt %; and a preferred range of the amount of the inositol phosphate(s) or salt(s) thereof be indicated by a combination of the upper and lower limits.

The composition of the present invention may be such that inositol phosphate(s) or salt(s) thereof are administered, for example, 10 mg to 15 g per administration, preferably 100 mg to 8 g per administration, more preferably 300 mg to 5 g per administration as the inositol phosphate(s), which may vary depending on the kind of inositol phosphate(s) or salt(s) thereof. Examples of the lower limit of the dose of inositol phosphate(s) or a salt(s) thereof per administration include 10 mg, 100 mg, 300 mg, 500 mg, and 600 mg as the inositol phosphate(s); and examples of the upper limit include 15 g, 10 g, 8 g, 5 g, 3 g, 2 g, 1 g, and 600 mg as the inositol phosphate(s); and a preferred range of the dose of inositol phosphate(s) or salt(s) thereof per administration may be indicated by a combination of the upper and lower limits.

The composition of the present invention may be such that inositol phosphate(s) or salt(s) thereof are administered, for example, 10 mg to 15 g per day, preferably 100 mg to 8 g per day, more preferably 300 mg to 5 g per day as the inositol phosphate(s), which may vary depending on the kind of inositol phosphate(s) or salt(s) thereof. Examples of the lower limit of the dose of inositol phosphate(s) or a salt(s) thereof per day include 10 mg, 100 mg, 300 mg, 500 mg, and 600 mg as the inositol phosphate(s); and examples of the upper limit include 15 g, 10 g, 8 g, 5 g, 3 g, 2 g, 1 g, and 600 mg as the inositol phosphate(s); and a preferred range of the dose of inositol phosphate(s) or salt(s) thereof per day may be indicated by a combination of the upper and lower limits. The amount of inositol phosphate(s) or salt(s) thereof which may be administered per day, may be administered in a single administration or in multiple divided administrations (for example, twice, three times, four times, and five times).

The amount of inositol phosphate(s) or salt(s) thereof contained in the composition of the present invention can be analyzed by conventional analytical method(s) known to those skilled in the art. Examples thereof include, but are not limited to, an ion chromatography method and a vanadomolybdic acid absorbance method.

The timing of intake of the composition of the present invention is not particularly limited, but the composition is preferably taken during a meal or within 30 minutes before or after a meal.

The composition of the present invention is preferably formulated as an oral dosage form, and the formulation is not particularly limited, but may be for example, tablets, granules, capsules, powders, chewable tablets, sweets (Cookies, biscuits, chocolate confectioneries, chips, cakes, gums, candies, gummies, buns, yokan (sweet bean jelly), puddings, jellies, yogurt, ice cream, sherbet, etc.), bread, noodles, rice, cereal foods, beverages (liquid preparations, soft drinks, carbonated drinks, nutritional drinks, powdered drinks, fruit drinks, milk drinks, jelly drinks, etc.), soups (powder, freeze-dry), miso soups (powder, freeze-dry), and conventional food forms.

The composition of the present invention may be formulated into orally administered formulations by adding pharmaceutically acceptable base(s), carrier(s), additive(s) usable in food, etc., in addition to inositol phosphate(s) or salt(s) thereof. It is desirable that ingredient(s) other than inositol phosphate(s) or salt(s) thereof used in the composition of the invention do not impair the stability of the inositol phosphate(s), and that they do not impair the intended effect(s) of the composition of the invention.

The composition of the present invention may be a food and drink or a pharmaceutical composition, and may be used as a food and drink, for example Foods with Functional Claims, Food for specified health uses, a health food, a nutritional supplement (supplement), a food for medical use, etc.

In the present invention, "purine body absorption" means that purine bodies (purine bases, purine nucleosides, purine nucleotides, or nucleic acids containing purine nucleotide bases (e.g., oligonucleotides, polynucleotides)) are absorbed into the body, after metabolism required depending on the form of purine body.

In the present invention, "inhibiting purine body absorption" means that the amount of purine bodies (for example, dietary purine bodies) absorbed into the body (for example, absorbed into the body through the intestinal tract) is relatively reduced. The "inhibiting purine body absorption" includes, for example, inhibition of alkaline phosphatase and/or 5'nucleotidase, which prevent conversion of purine nucleotides to purine nucleosides (This results in less purine bodies being absorbed into the body).

In the present invention, "dietary purine body (dietary purine bodies)" means purine bodies derived from an ingested food or drink.

In the present invention, "a purine body that can be absorbed through the intestinal tract" include purine base(s) and purine nucleoside(s).

In the present invention, "inhibiting purine nucleotide metabolism" means inhibiting the conversion of purine nucleotide(s) to purine nucleoside(s).

In the present invention, "inhibiting phosphatase" means inhibiting phosphatase activity involved in purine metabolism, for example includes inhibiting alkaline phosphatase and/or 5' nucleotidase.

In the present invention, the term "inhibiting uric acid level elevation" means suppressing an excessive rise in the uric acid level, and includes, for example, lowering or alleviating the rise in the serum uric acid level in a person with a high serum uric acid level (including a person whose uric acid level is in normal but a little high), and maintaining the serum uric acid level, or preventing or alleviating the rise in the serum uric acid level, in a person with a normal or low serum uric acid level.

In the present invention, "improving blood pressure" means suppressing an excessive rise in blood pressure, and includes, for example, decreasing or alleviating blood pressure elevation in a person with a high blood pressure (including a person whose blood pressure is in normal but a little high), and maintaining blood pressure, preventing or alleviating blood pressure elevation in a person with a normal blood pressure or a little low blood pressure.

In the present invention, "improving blood glucose level" means that an excessive rise in blood glucose level is suppressed, and includes, for example, lowering or alleviating the rise in the blood glucose level in a person with a high blood glucose level (including a person whose level is in normal but a little high), and maintaining the blood glucose level and preventing or alleviating the rise in the blood glucose level in a person with a normal blood glucose level or a little low blood glucose level.

In the present invention, "improving liver function" means that liver function is improved, for example, the function may be indicated by an indicator (for example, AST: aspartate aminotransferase). For example, "improving liver function" includes lowering or alleviating the rise in blood AST level in a person with a high blood AST level (including a person whose level is in normal but a little high), and maintaining blood AST level, preventing or alleviating the rise in blood AST level in a person with a normal or a little low blood AST level, In the present invention, "controlling serum iron level" means inhibiting an excessive increase or decrease in serum iron levels, including, for example, decreasing or alleviating the rise in serum iron level in a person with a high serum iron level (including a person whose level is in normal but a little high); increasing serum iron level or alleviating the decrease in serum iron level in a person with low serum iron level (including a person whose level is in normal but a little low); maintaining serum iron level, preventing an increase or decrease in serum iron level, or alleviating an increase or decrease in serum iron level in a person with normal serum iron level.

In the present invention, "promoting calcium absorption" means that absorption of calcium through the intestinal tract is promoted. In the present invention, the term "promoting calcium absorption" includes an increase in the blood concentration of active vitamin D (1, 25-(OH)$_2$-D) that promotes absorption of calcium through the intestinal tract.

A composition for inhibiting purine body absorption, a composition for inhibiting purine nucleotide metabolism, a composition for inhibiting phosphatase, a composition for inhibiting uric acid level elevation, a composition for improving blood pressure, a composition for improving blood glucose level, a composition for improving liver function, a composition for controlling serum iron level, or a composition for promoting calcium absorption, of the present invention may be formulated as a formulation to be used for these intended uses (inhibiting purine nucleotide metabolism, inhibiting phosphatase, inhibiting uric acid level elevation, improving blood pressure, improving blood glucose level, improving liver function, controlling serum iron level, or promoting calcium absorption). The intended use of the formulation may be indicated on the product itself, packaging, instructions, pamphlets, containers, advertising, advertising materials for the sales floor such as POP, other documents, electromagnetic methods (Internet, etc.), etc. For example, the following products stating the intended use or expressions that conjure/analogize the intended use: drugs (including quasi-drugs); Food for specified health uses, food with nutrient function claims, food with functional claims, etc., for which indications have been approved by designated organizations; ordinary foods and drinks are also within the scope of the present invention.

For example, with respect to a composition for inhibiting purine body absorption or a composition for inhibiting uric acid level elevation of the present invention, foods and drinks, etc., in which expressions such as "For those who are concerned about purine bodies in meals", "fight purine bodies", "For those who tend to eat meals with a lot of purine bodies", "For those concerned about postprandial uric acid levels", etc., which conjure/analogize inhibiting purine body absorption or inhibiting uric acid level elevation, are also within the scope of the present invention.

With regard to a composition for improving blood pressure of the present invention, foods and drinks, etc. in which expressions such as "suitable for a person with a little high blood pressure", "support healthy blood pressure", "capable of lowering a little high blood pressure", "For a person who is concerned about blood pressure", "maintain normal blood pressure", "improve blood pressure", and the like which recall/conjure improving blood pressure are described are also included in the scope of the present invention.

With regard to a composition for improving blood glucose level of the present invention, foods and drinks, etc., in which expressions such as "Suitable for a person who is concerned about their blood glucose level", "moderate the rise in blood glucose level", "keep a little high blood glucose level in normal", "for a person with a little high blood glucose level", etc., which recall/conjure improving blood glucose level are described are also included in the scope of the present invention.

With regard to a composition for improving liver function of the present invention, foods and drinks, etc. in which expressions such as "Maintaining a healthy liver" and "for people with a higher figure of liver function indicator" which recall/conjure improving liver function are described are also included in the scope of the present invention.

With regard to a composition for controlling serum iron level of the present invention, foods and drinks, etc. in which expressions such as "For a person who is concerned about iron deficiency" and "For the prevention of anemia" which recall/conjure controlling serum iron level are described are also included in the scope of the present invention.

With regard to a composition for promoting calcium absorption of the present invention, foods and drinks, etc. in which expressions such as "contribute to bone health", "maintenance of bone components", "help bone metabolism", "maintain strong bones", "To prevent osteoporosis", and the like which recall/conjure promoting calcium absorption are described are also included in the scope of the present invention.

In the composition (for example, liquid preparation) containing inositol phosphate(s) or salt(s) thereof, the bitterness and harsh taste of the inositol phosphate(s) or salt(s) thereof (especially phytic acid or salt(s) thereof) are improved by adding calcium lactate. The calcium lactate is preferably added in a weight ratio of inositol phosphate(s) (the amount of salt(s) of the inositol phosphate(s) is converted as the amount of inositol phosphate):calcium lactate=1:0.2 to 1:0.5 (more preferably 1:0.26 to 1:0.4).

The subject of administration of the composition of the present invention is not particularly limited, but is preferably human. The composition of the present invention may be taken by a healthy person for daily health in addition to a person being concerned about uric acid level, blood pressure, blood glucose level, liver function, anemia or bone health.

EXAMPLE

The present invention is explained in further detail with reference to Formulation Examples and Test Examples. However, the scope of the invention is not limited to these Examples. Phytic acid used in the Formulation Examples and Test Examples was purchased a commercial product that complied with the liquid product or powder product of Voluntary specifications of existing food additives".

[Formulation Example 1] Beverage (pH 3.0)

| | |
|---|---|
| Phytic acid | 600 mg |
| Dextrin | 1000 mg |
| Erythritol | 800 mg |
| Acidulant | Suitable quantity |
| Calcium lactate | Suitable quantity |
| Fragrance | Suitable quantity |
| Sweetener | Suitable quantity |
| Water | Suitable quantity |
| Total | 50 mL |

The beverage of the above formula is prepared according to a conventional method.

Test Example 1: Purine Nucleotide Metabolism Inhibitory Activity of Phytic Acid

The rat small intestine powder contains alkaline phosphatase and 5'nucleotidase as the main digestive enzymes. The inhibition of metabolism of purine nucleotides to purine nucleosides by phytic acid was investigated.
(Test Method)
A 100 mg/mL of solution of rat small intestine powder (Clare Japan, Inc.) in the assay buffer (2.37% aqueous solution of Trizma® maleate (Sigma-Aldrich)) was used as the enzyme solution. Inosine monophosphate (IMP) (Sigma-Aldrich) (9 mM) in the assay buffer was used as the substrate solution.

Phytic acid and the assay buffer were mixed, and the pH was adjusted to 6.2 to 6.4 with sodium hydroxide to obtain the sample solutions of each concentration. The control solution was prepared by adjusting the assay buffer to pH 6.2 to 6.4 with sodium hydroxide.

Enzymatic reaction was performed using a 96 well plate (Thermo Fisher Scientific) in the following manner.

The sample solution or control solution (100 µL/well), the substrate solution (100 µL/well), and the enzyme solution (100 µL/well) were added, and the enzyme reaction was performed at 37° C. for 30 minutes. A 20 µL aliquot of the reaction solution was transferred to multi-screen HTS HV (Merck Millipore), and the reaction was stopped by adding the stop solution (0.33 M $HClO_4$, 180 µL/well). Centrifugation (1080×g for 10 minutes at room temperature) was performed, and the filtrate was subjected to high performance liquid chromatography (HPLC) to determine the amounts of inosine monophosphate and inosine.

The analytical conditions of HPLC are shown below.
Detector: Nanospace 3002 (SHISEIDO Co., Ltd.)
Column: COSMOSIL PAQ (4.6 mm I.D.×150 mm, NACALAI TESQUE, INC.)
Mobile phase: 50 mM $KH_2PO_4$ (pH 7.5)
Flow rate: 1.0 mL/min. Detection wavelength: 254 nm.
Column temperature: 35° C.
Sample injection volume: 10 μL
(Result)
Results are shown in FIG. 1.
Similar activity was also suggested for Inositol monophosphate, Inositol 1,4-bisphosphate, Inositol 1,4,5-trisphosphate, Inositol 1,4,5,6-tetrakisphosphate, Inositol 1,3,4,5,6-pentakisphosphate, and Inositol 1,2,3,4,5,6-hexakisphosphate.

Figure 2:
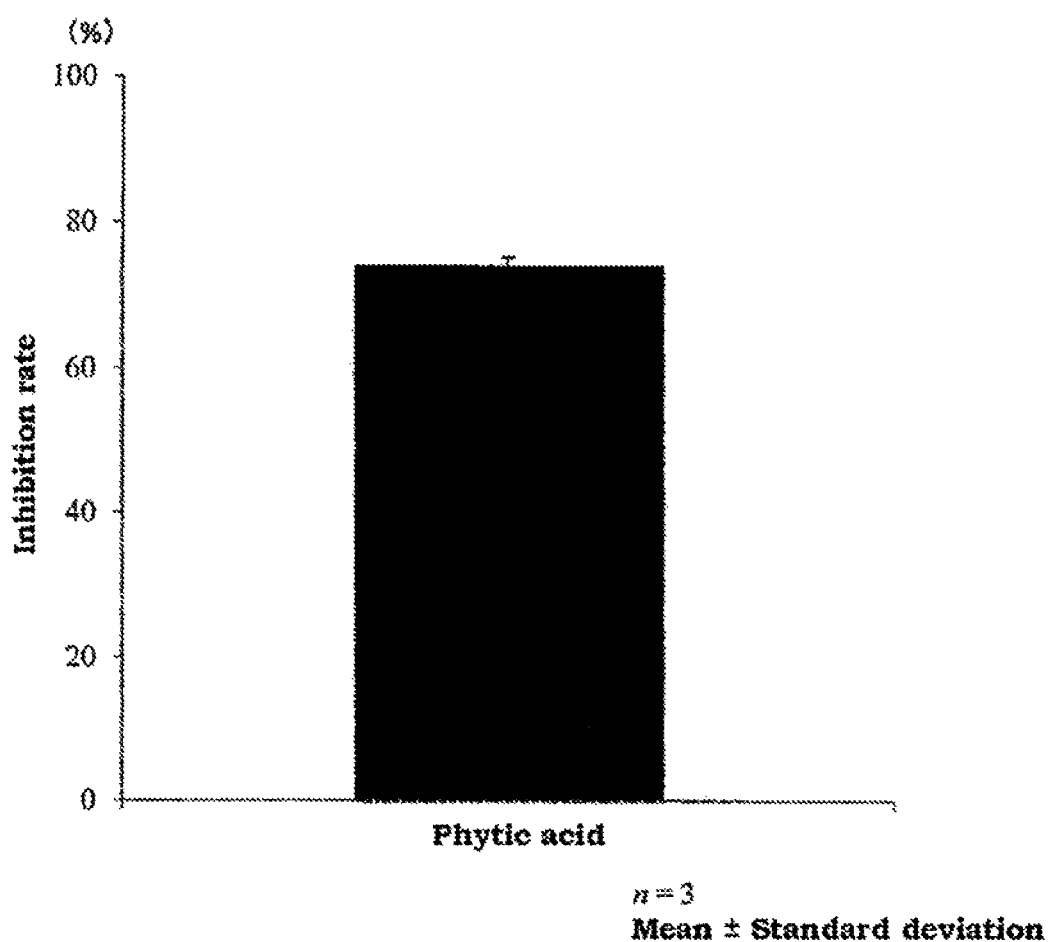
FIG. 2 shows the rate of metabolism inhibition of inosine monophosphate to inosine by phytic acid using alkaline phosphatase.

Test Example 2: Alkaline Phosphatase Inhibitory Effect of Phytic Acid (Test Method)
Phosphatase, Alkaline, Calf Intestine (Merck) dissolved in the assay buffer (2.37% aqueous solution of Trizma® maleate (Sigma-Aldrich)) at 5.0 U/mL was used as the enzyme solution.
Inosine monophosphate (IMP) (Sigma-Aldrich) dissolved in the assay buffer at 9 mM was used as the substrate solution.
Phytic acid and the assay buffer were mixed, and the pH was adjusted to 6.2 to 6.4 with sodium hydroxide to obtain a sample solution (10 mg/mL). The control solution was prepared by adjusting the assay buffer to pH 6.2 to 6.4 with sodium hydroxide.
Enzymatic reaction was performed using a 96 well plate (Thermo Fisher Scientific) in the following manner.
The sample solution or control solution (100 μL/well), the substrate solution (100 μL/well), and the enzyme solution (100 μL/well) were added, and the enzyme reaction was performed at 37° C. for 30 minutes. A 20 μL aliquot of the reaction solution was transferred to multi-screen FITS HV (Merck Millipore), and the reaction was stopped by adding the stop solution (0.33 M $HClO_4$, 180 μl/well). Centrifuge (1080×g for 10 minutes at room temperature) was performed, and the filtrate was subjected to high performance liquid chromatography (HPLC) to determine the amounts of inosine monophosphate and inosine.
The analytical conditions of HPLC are shown below.
Detector: SPD-M 30 A (Shimadzu Corporation)
Column: COSMOSIL PAQ (4.6 mm I.D.×150 mm, NACALAI TESQUE, INC)
Mobile phase: 50 mM $KH_2PO_4$ (pH 7.5)
Flow rate: 1.0 mL/min. Detection wavelength: 254 nm.
Column temperature: 35° C.
Sample injection volume: 10 μL
(Result)
The results are shown in FIG. 2.

Test Example 3: Inhibitory Effect of Phytic Acid on Purine Absorption in Humans (Test Method)
The subjects were healthy male and female adults aged 20 years or older and younger than 65 years with a fasting serum uric acid level of less than 7 mg/dL at a prior health check-up, and postmenopausal women (24 men, 24 women, 48 total). The study design was a randomized, single-blind, crossover controlled trial.

Figures 1, 3:
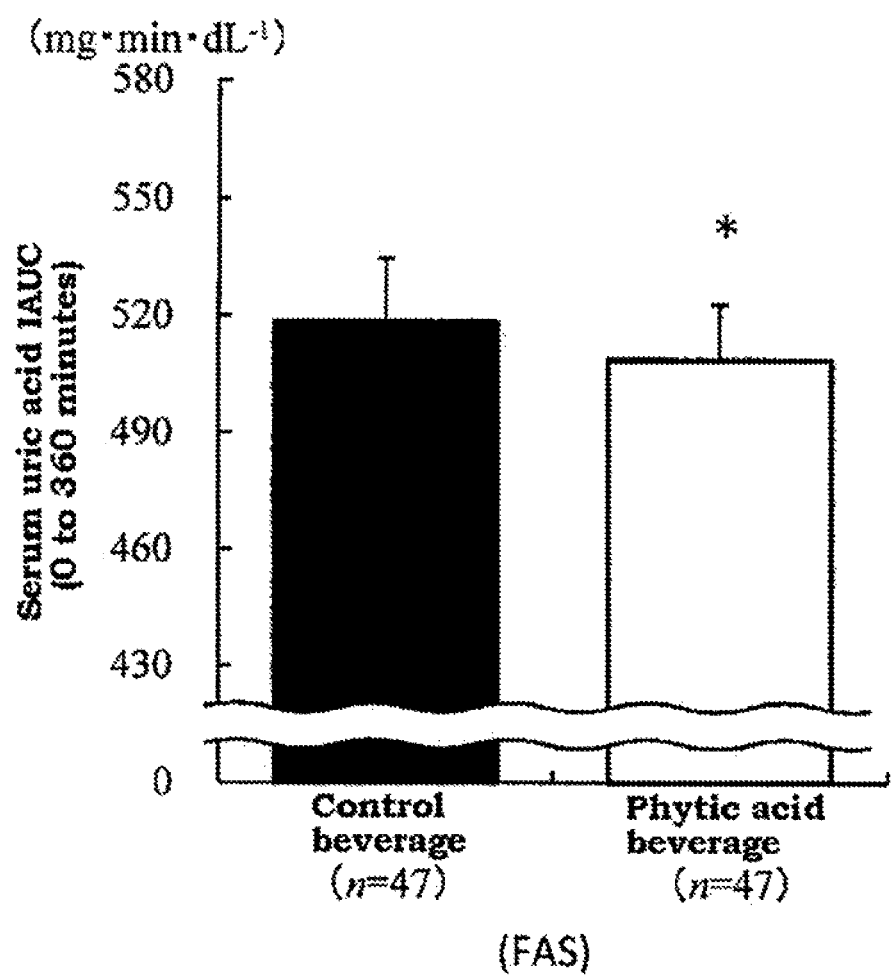
Figures 2, 3:
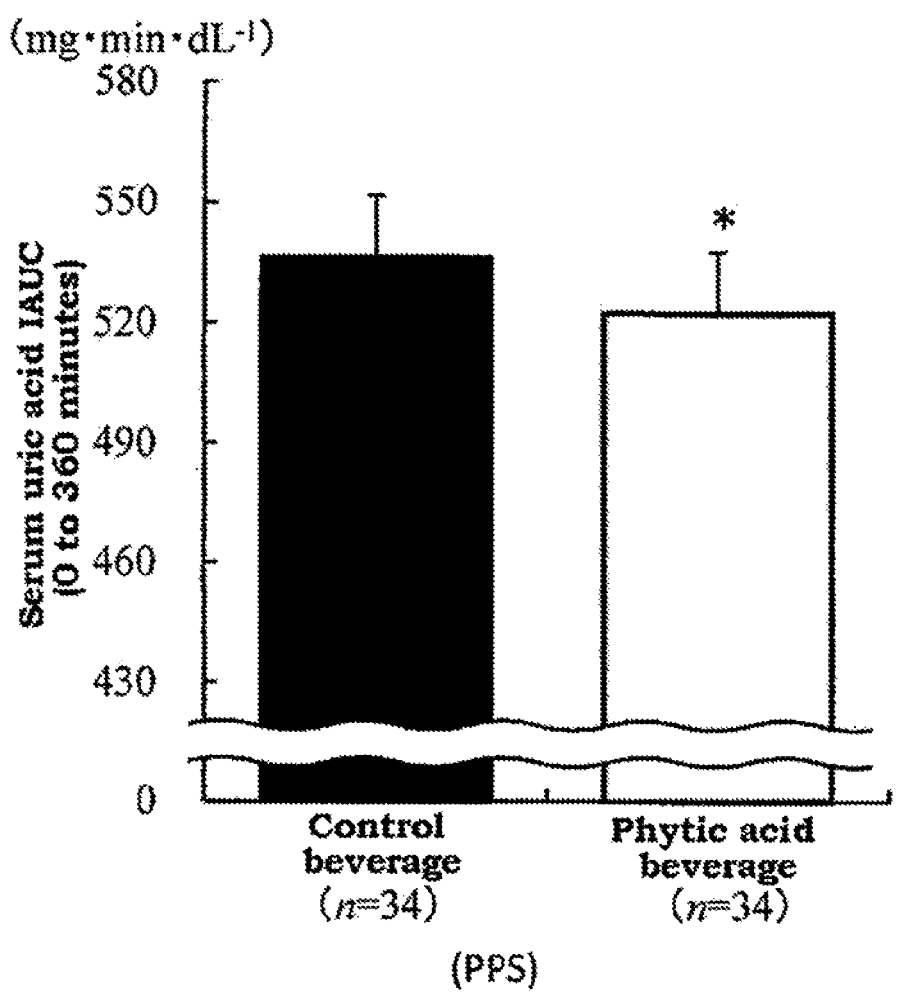
Figure 3:
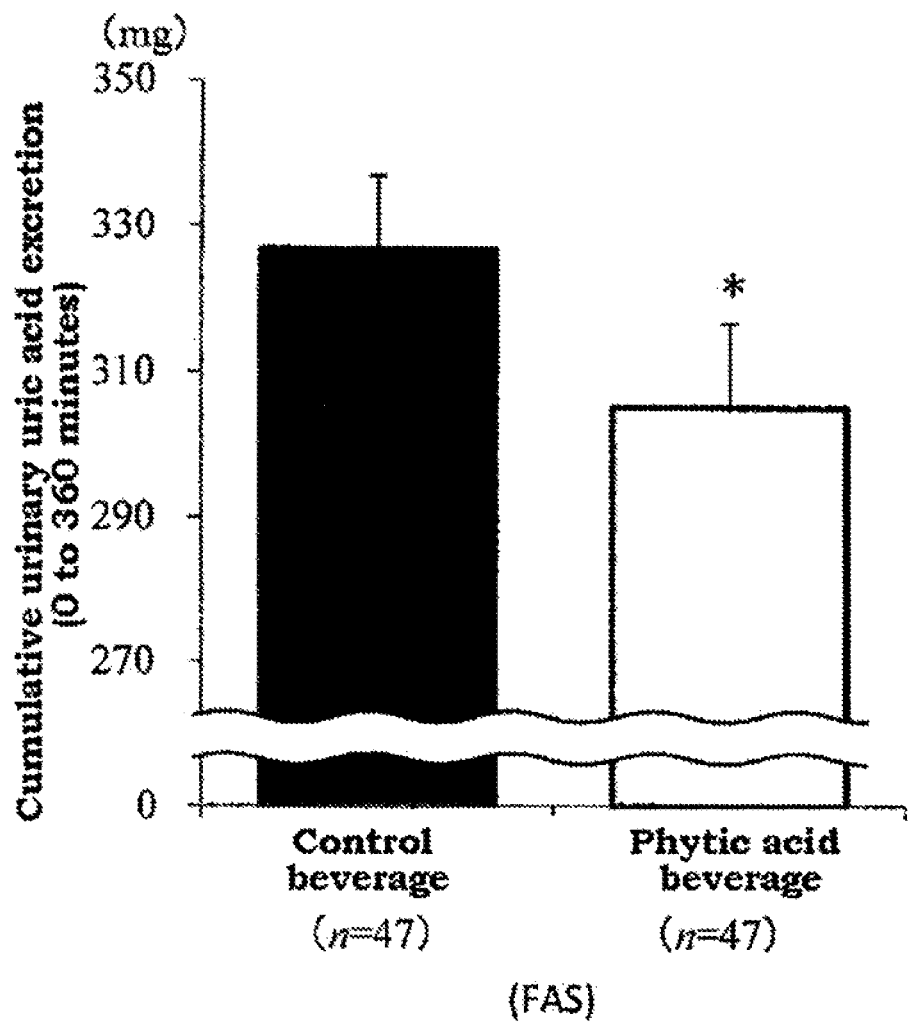

After an overnight fast, the subjects ingested 50 ml of a test beverage (a phytic acid beverage containing 600 mg of phytic acid or a control beverage which is a mineral water), a purine-loaded diet (Rice 200 g, lean tuna about 200 g (800 mg as a purine nucleotide equivalent), dark soy sauce 5 g), and a purine body beverage (0.5 g of a commercial seasoning containing equal amounts of sodium 5'-inosinate and sodium 5'-guanylate, dissolved in 150 mL of mineral water) simultaneously (within 20 minutes in principle) at 9:00. At 10:00, 11:00, and 13:00, 100 ml of mineral water was ingested, and blood and urine samples were taken before and 30, 60, 120, 240, and 360 minutes after ingestion of the test beverage. Serum uric acid levels (mg/dL) and urinary uric acid levels (mg/dL) were measured at an analysis contractor.
The primary endpoint was serum uric acid IAUC (0 to 360 minutes), and the secondary endpoint was a cumulative urinary uric acid excretion (0 to 360 minutes). A variance analysis (test beverage, timing, group and subject as factors) considering a crossover design with the fasting serum uric acid level before intake of the test beverage as a covariate was performed, and the error variance was used to t-test the difference between the control and phytic acid beverages. A two-sided test was performed with a significance level of 5%. FAS (full analysis set), which included subjects who had ingested the test food at least once, and PPS (per protocol set), which excluded subjects who did not meet the protocol, were analyzed. The PPS analysis was used for the primary endpoint analysis.
(Result)
The results are shown in FIG. 3.
The primary endpoint, serum uric acid level IAUC, was significantly lower in the phytic acid beverage compared with the control beverage in FAS and PPS analyses, which shows that the postprandial elevation of serum uric acid level was significantly suppressed. In addition, the secondary endpoint, cumulative urinary uric acid excretion, was significantly lower in the phytic acid beverage compared with the control beverage in FAS analysis, which shows that urinary uric acid excretion was significantly decreased.
Possible mechanisms of effect of phytic acid are that phytic acid affect the followings:
(1) dietary purine absorption;
(2) Uric acid production from purine bodies; and
(3) Urinary excretion of uric acid.
It is known that most of the orally ingested phytic acid is excreted without being absorbed through the intestine (Non-Patent Documents 5 and 6). According to Non-Patent Document 5, the blood phytic acid concentration following ingestion of 1,400 mg of sodium phytate (1,000 mg as phytic acid) is 0.12 mg/L (0.181 μM) at the maximum, and it is considered that the blood concentration of phytic acid in this study involving ingestion of 600 mg of phytic acid was lower compared with that. It is considered that the extremely low blood concentration of phytic acid in this study does not affect the metabolic system such as uric acid formation from purine bodies ((2) above) or urinary excretion of the formed uric acid ((3) above).
As described above, in the case where phytic acid inhibits the metabolism of xanthine to uric acid by inhibiting xanthine oxidase activity, the $IC_{50}$ is as high as about 30 mM (19.8 g/L) (Non-Patent Document 4), and therefore, the blood extremely low concentration of phytic acid in this test cannot inhibit xanthine oxidase activity.
In addition, the results of Examples 1 and 2 suggest that phytic acid inhibits the conversion of purine nucleotides into purine nucleosides (purine nucleosides is absorbable through the intestinal tract), in the gastrointestinal tract and inhibits the absorption of dietary purine bodies.

Therefore, the suppression of the rise in the serum uric acid level and the decrease in the urinary uric acid excretion in this study are considered to be due to the suppression of the absorption of dietary purine bodies by phytic acid.

Test Example 4: Effects of Phytic Acid on Blood Pressure, Blood Glucose, Liver Function, Calcium Metabolism, and Serum Iron in Humans (High Intake Test)

The subjects (48 healthy adults: 20 to 65 years of age, 16 men, 16 premenopausal women, and 16 postmenopausal women) ingested 5 bottles per day (or 3 to 5 bottles per day depending on the subject's capacity) of test beverage. The test beverage contains 600 mg of phytic acid per bottle (50 mL). The duration of intake was 5 weeks. The first week being a time period to determine each subject's tolerable volume of test beverage, during which time the subjects ingested test beverages while increasing one bottle daily (Up to 5 bottles per day). If 5 bottles/day could not be taken due to taste, volume, etc., the intake volume was determined by each subject, and the intake volume on day 7 was taken as the tolerable volume for each subject, and each subject ingested this tolerable volume (3 to 5 bottles per day) during the remaining study period (4 weeks). Before and 3 weeks, 5 weeks, and 7 weeks (i.e. 2 weeks after the last intake) after the start of the intake, blood pressure of fasting was measured and blood of fasting was collected. The collected blood was measured for each test item by an analysis contractor. Tests for blood pressure, blood glucose, AST, and serum iron compared to 0 week were performed with a paired t-test, and tests for 1, 25-(OH)$_2$-D compared to 0 week were performed with one-way ANOVA followed by Dunnet's multiple comparison method. A two-sided test was performed with a significance level of 5%. The analysis included 44 subjects excluding 2 subjects who withdrew their consent and 2 subjects who were unable to take more than 3 bottles of the test beverage.

(Low Intake Test)

Subjects (39 healthy adults: 20 to 65 years of age, 13 men, premenopausal women, and 13 postmenopausal women) ingested 1 bottle of a test beverage per day for 12 weeks. The test beverage contains 600 mg of phytic acid per bottle (50 mL). Before and 4 weeks, 8 weeks, 12 weeks, and 14 weeks (i.e. 2 weeks after the last intake) after the start of the intake, blood of fasting was collected. The collected blood was measured for each test item by an analysis contractor. Tests for each endpoint compared to 0 week were performed with a paired t-test. Two-sided test was performed with a significance level of 5%.

(Result)

1. Blood Pressure

Figures 3, 4:
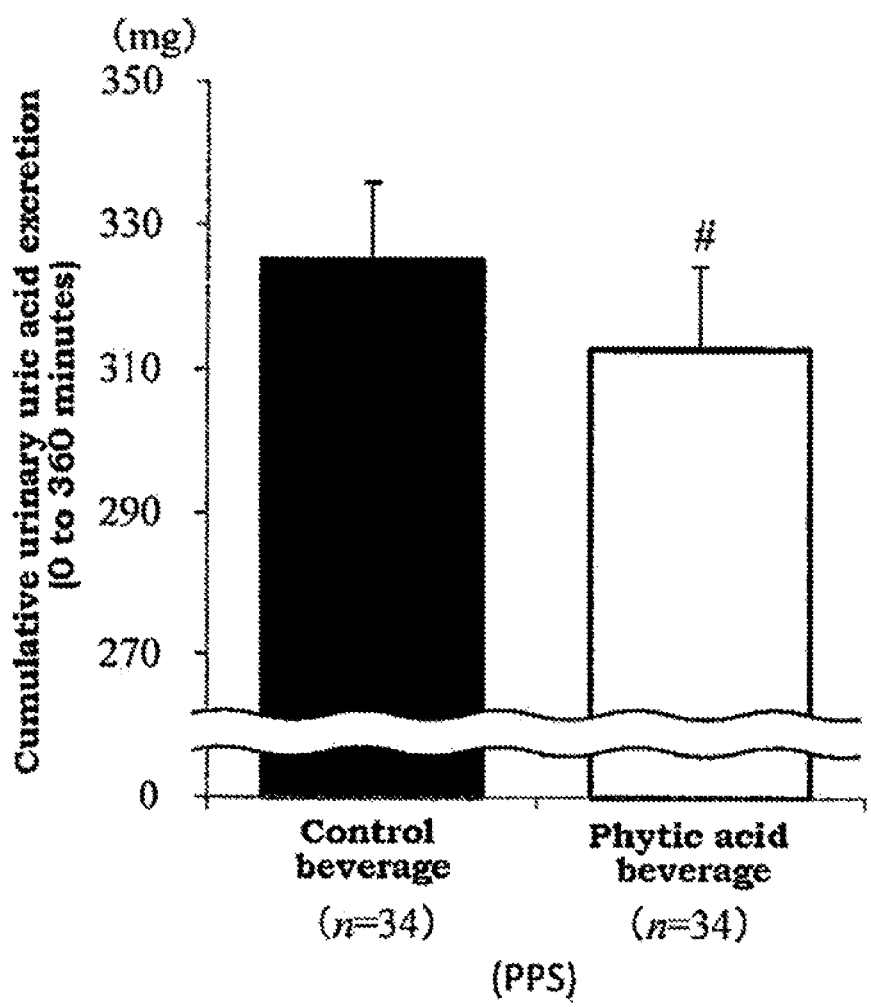
Figures 1, 4:
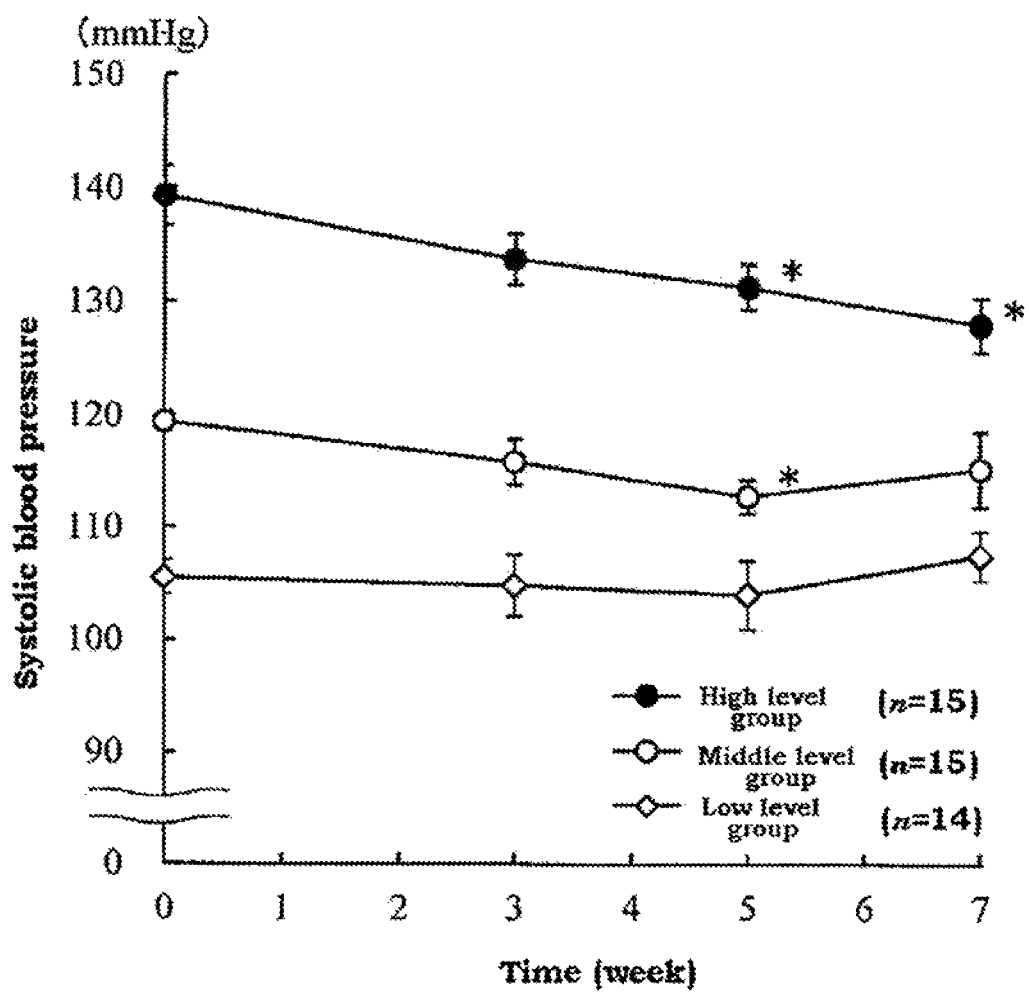
Figures 2, 4:
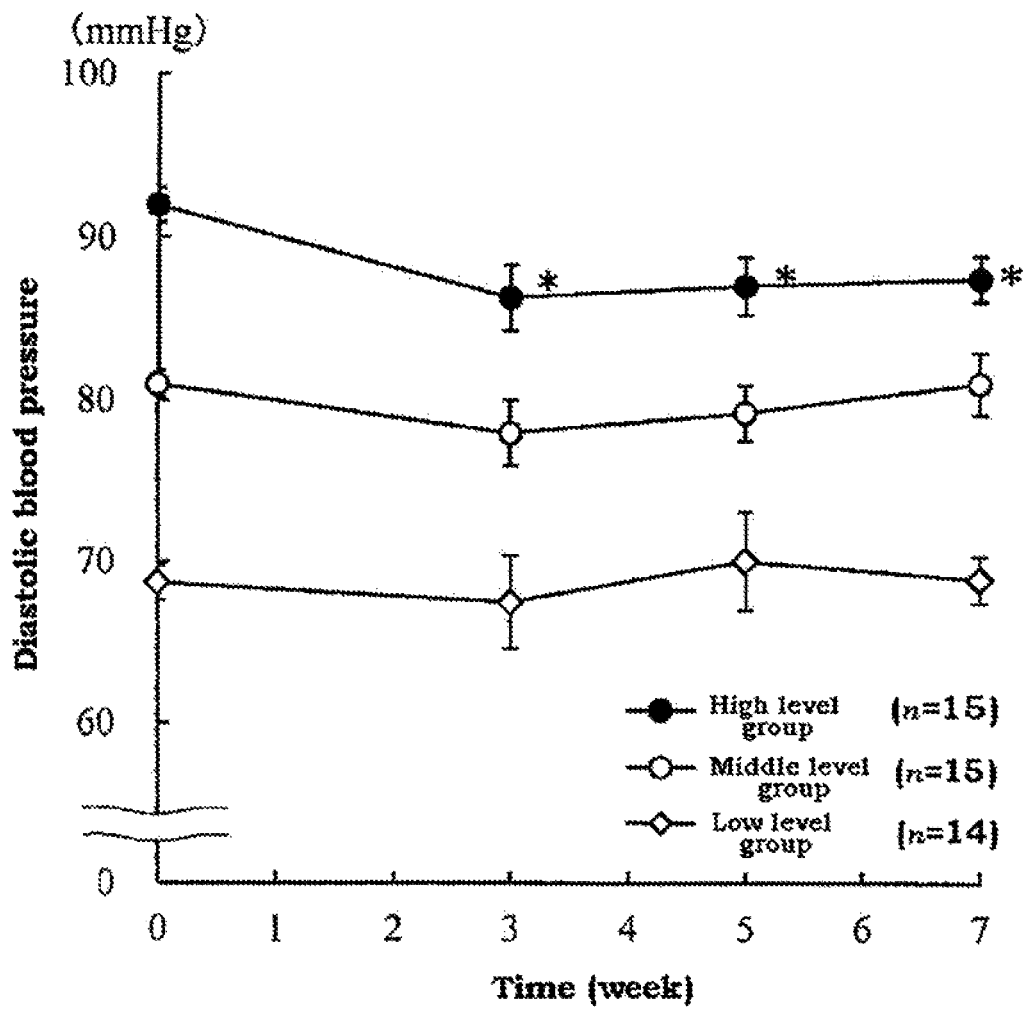

In the High intake test, subjects were divided equally into three groups according to systolic and diastolic blood pressures before the start of intake (0 Weeks), and the changes of the mean blood pressures of each group were examined. The results are shown in FIG. 4.

The ranges of systolic and diastolic blood pressures before the start of intake (0 week) for the subjects in each group are shown in Table 1.

TABLE 1

| | Systolic blood pressure | | Diastolic blood pressure |
|---|---|---|---|
| High level group | 126 or more | High level group | 86.3 or more |
| Middle level group | 115.5 to 126 | Middle level group | 73.8 to 86.3 |
| Low level group | 115.5 or less | Low level group | 73.8 or less |

As shown in FIG. 4:

A significant decrease in blood pressure was observed in the high systolic blood pressure group and the high diastolic blood pressure group;

In blood pressure of the middle systolic blood pressure group there was a significant change but it was not large, and in the middle diastolic blood pressure group there was no change in blood pressure; and there was no change in blood pressure in the low systolic blood pressure group and the low diastolic blood pressure group.

Guidelines for the management of hypertension 2014 defines the range of high normotension as systolic blood pressure of 130 to 139 and/or diastolic blood pressure of 85 to 89. The results suggest that intake of phytic acid lowers and improves blood pressure in subjects in the higher normotensive range, the so-called "person whose blood pressure is a little high".

2. Glucose Metabolism (Blood Glucose Level and HbA1c)

Figures 1, 5:
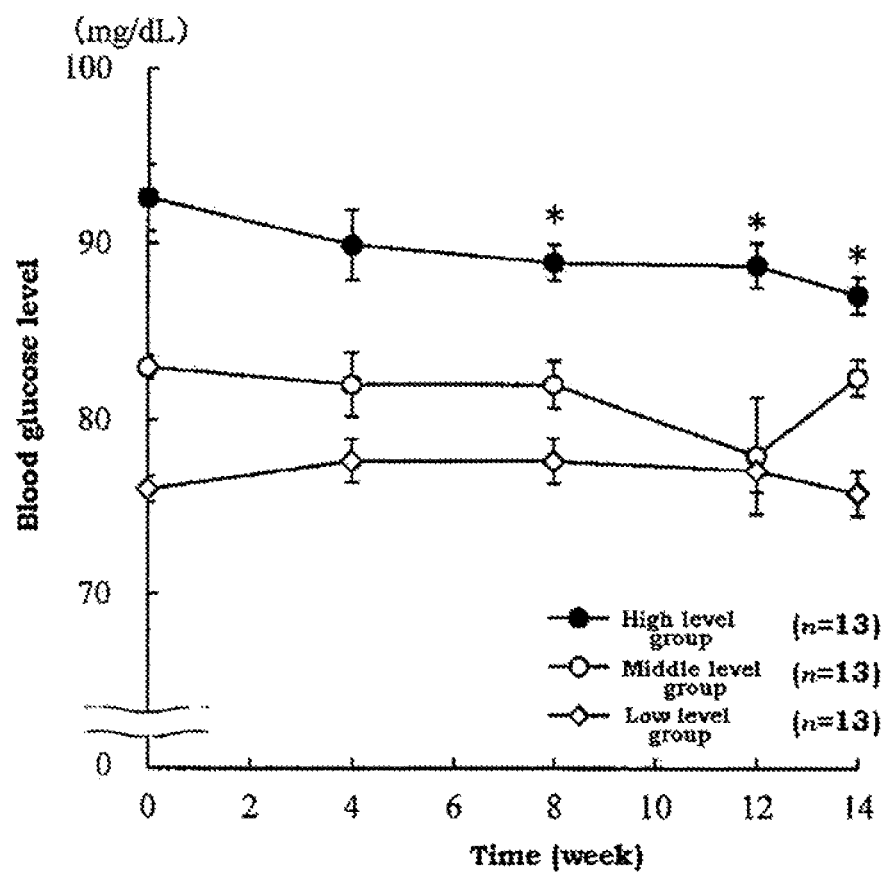
Figures 2, 5:
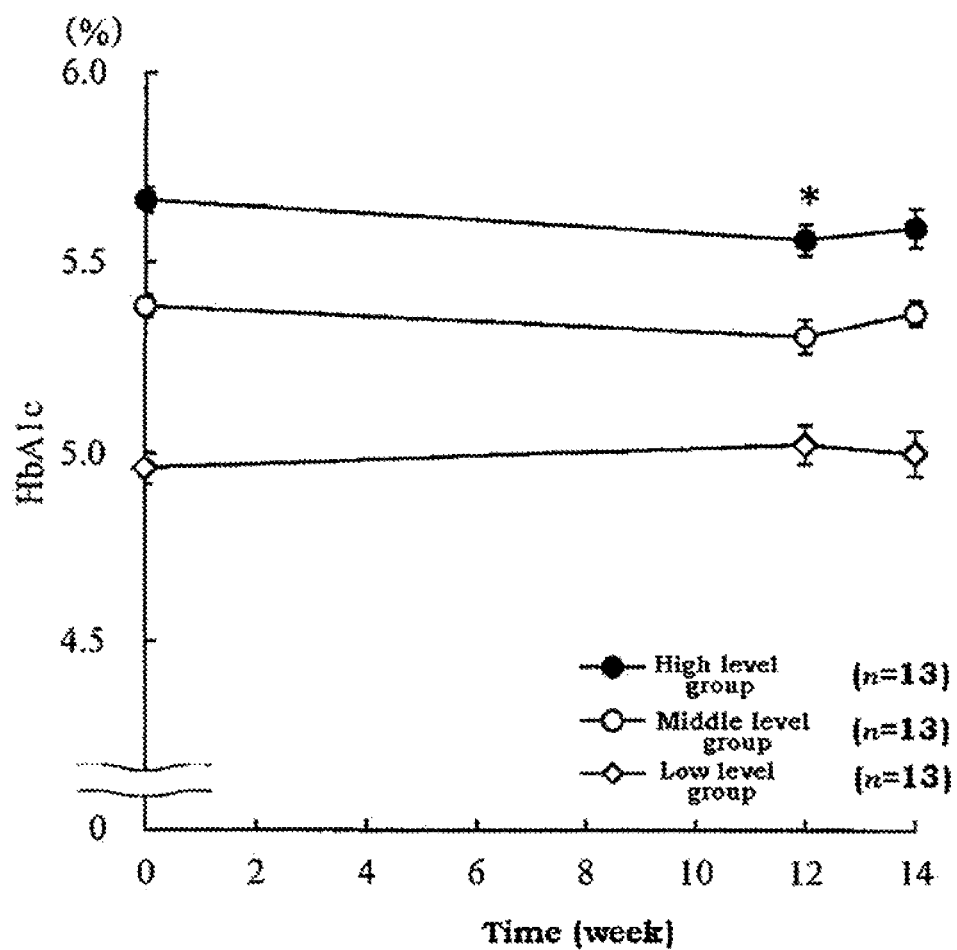

In the low intake test, subjects were divided equally into three groups according to the blood glucose and HbA1c levels before the start of intake (0 Weeks), and the changes in the mean blood glucose and HbA1c levels of each group were examined. The results are shown in FIG. 5.

The ranges of blood glucose and HbA1c levels before the start of intake (0 Weeks) for the subjects in each group are shown in Table 2.

TABLE 2

| | Blood glucose level | | HbA1c |
|---|---|---|---|
| High level group | 86 or more | High level group | 5.5 or more |
| Middle level group | 79 to 86 | Middle level group | 5.2 to 5.5 |
| Low level group | 79 or less | Low level group | 5.2 or less |

As shown in FIG. 5:

a significant decrease in blood glucose level was observed in the high blood glucose level group; and a significant decrease in HbA1c level was observed in the high HbA1c level group.

Japanese Clinical Practice Guideline for Diabetes defines the range of high-normal of blood glucose level is 100 to 109. The results suggests that the intake of phytic acid drink decreases the both levels of subjects who is within the normal range but a little high, the so-called "person whose blood glucose is a little high" and improves glucose metabolism.

3. Liver Function (AST)

Figure 6:
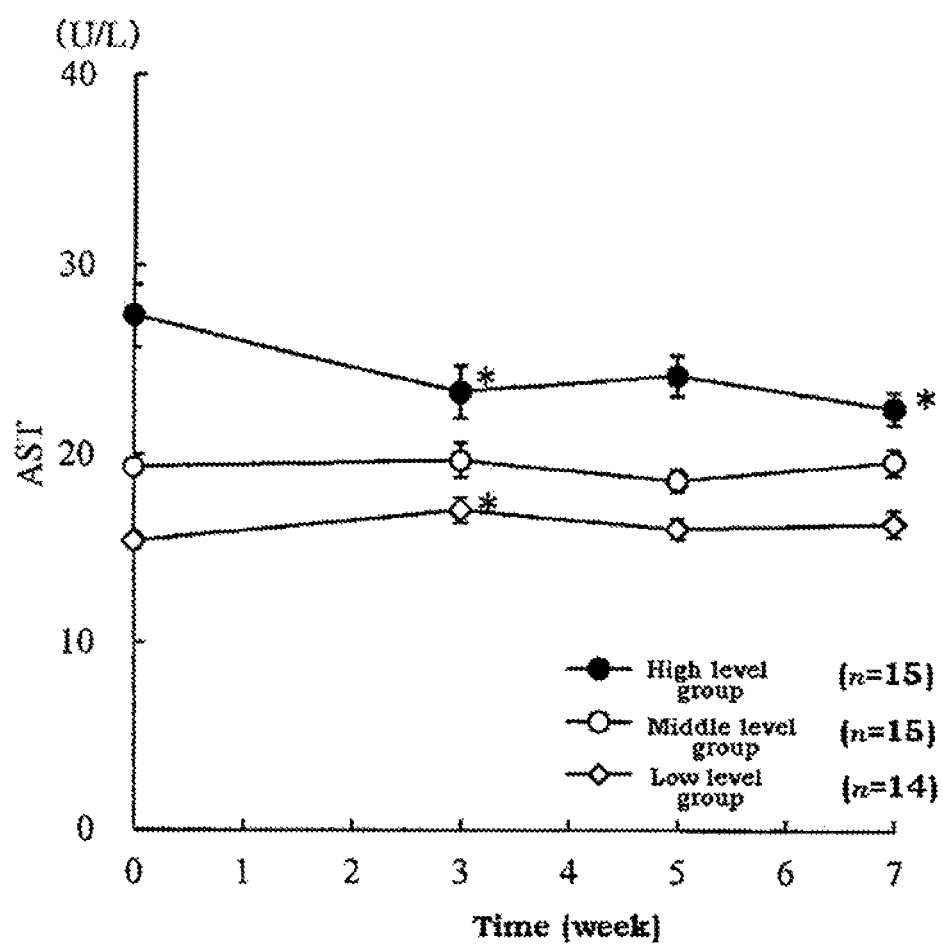
FIG. 6 shows the change in the mean values of AST in the high intake test.

In the High intake test, subjects were divided equally into three groups according to the AST level before the start of intake (0 Week), and the change in the mean AST level in each group was examined. The results are shown in FIG. 6.

The range of AST levels before the start of intake (0 Week) for the subjects in each group is shown in Table 3.

TABLE 3

|  | AST level |
|---|---|
| High level group | 21 or more |
| Middle level group | 17 to 21 |
| Low level group | 17 or less |

As shown in FIG. 6, in the high level group, significant decreases were observed after ingestion (3, 5, and 7 weeks) compared with before ingestion; and in the Low level group, a significant increase was observed after ingestion (3 Weeks) compared with before ingestion, but the change is not large.

It was suggested that in a person with high AST levels the intake of phytic acid decreases AST and improves liver function.

4. Serum Iron Level

Figures 2, 7:
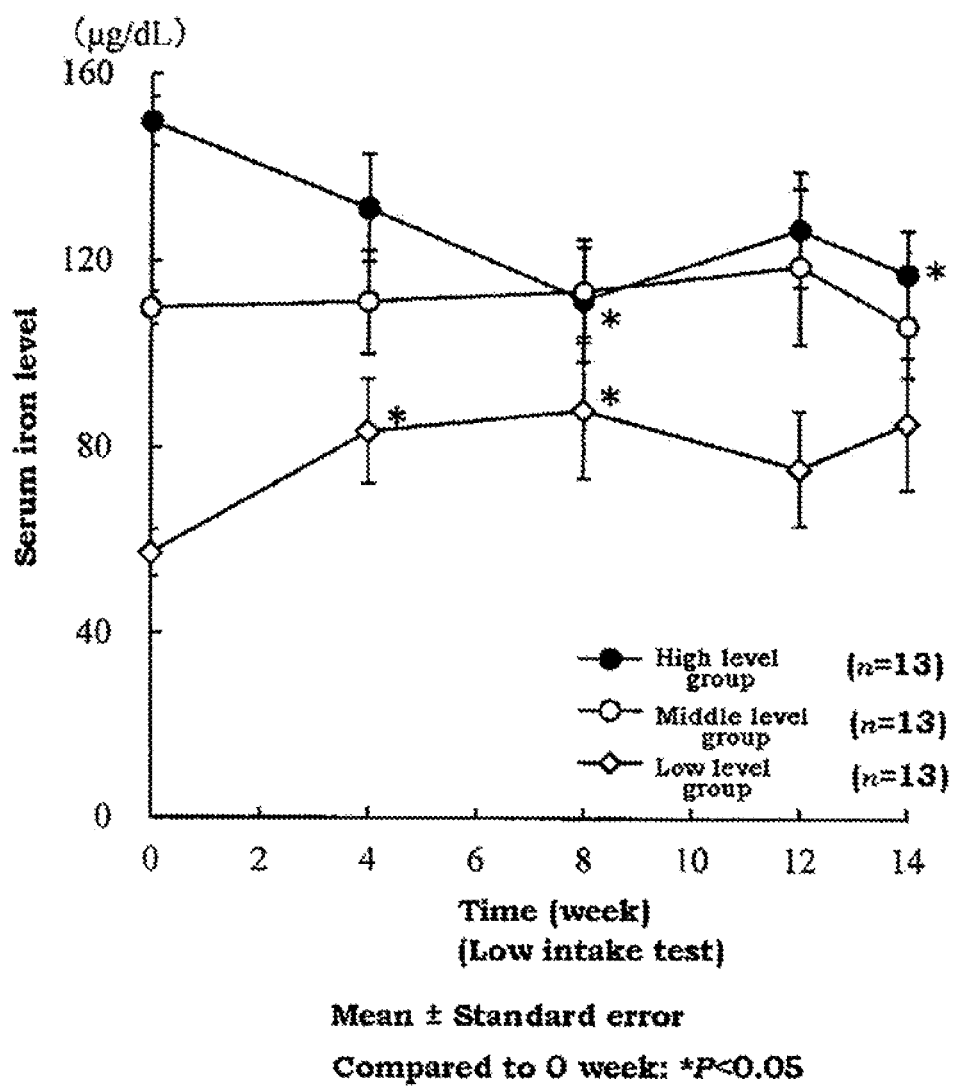

In each of the high and low intake tests, subjects were divided equally into three groups according to the serum iron level before the start of intake (0 Weeks), and the change in the mean serum iron level of each group was examined. The results are shown in FIG. 7.

The ranges of serum iron levels before the start of intake (0 Weeks) for the subjects in each group are shown in [Table 4-1] and [Table 4-2].

TABLE 4-1

| High intake test | Serum iron level |
|---|---|
| High level group | 117 or more |
| Middle level group | 79 to 117 |
| Low level group | 79 or less |

TABLE 4-2

| Low intake test | Serum iron level |
|---|---|
| High level group | 132 or more |
| Middle level group | 90 to 132 |
| Low level group | 90 or less |

As shown in FIG. 7, for both tests:

in the high level groups, significant decreases were observed;

there were no large changes in the middle level groups; and in the low level groups, significant rises were observed.

It was suggested that intake of phytic acid lowers serum iron level in a person with a high serum iron level and increases serum iron level in a person with a low serum iron level, and thereby improves serum iron level.

5. Calcium Absorption

Active vitamin D (1,25-$(OH)_2$-D) is known to promote intestinal absorption of calcium. The change in the mean values of 1,25-$(OH)_2$-D was examined in the high intake test. The results are shown in FIG. 8.

Figure 8:
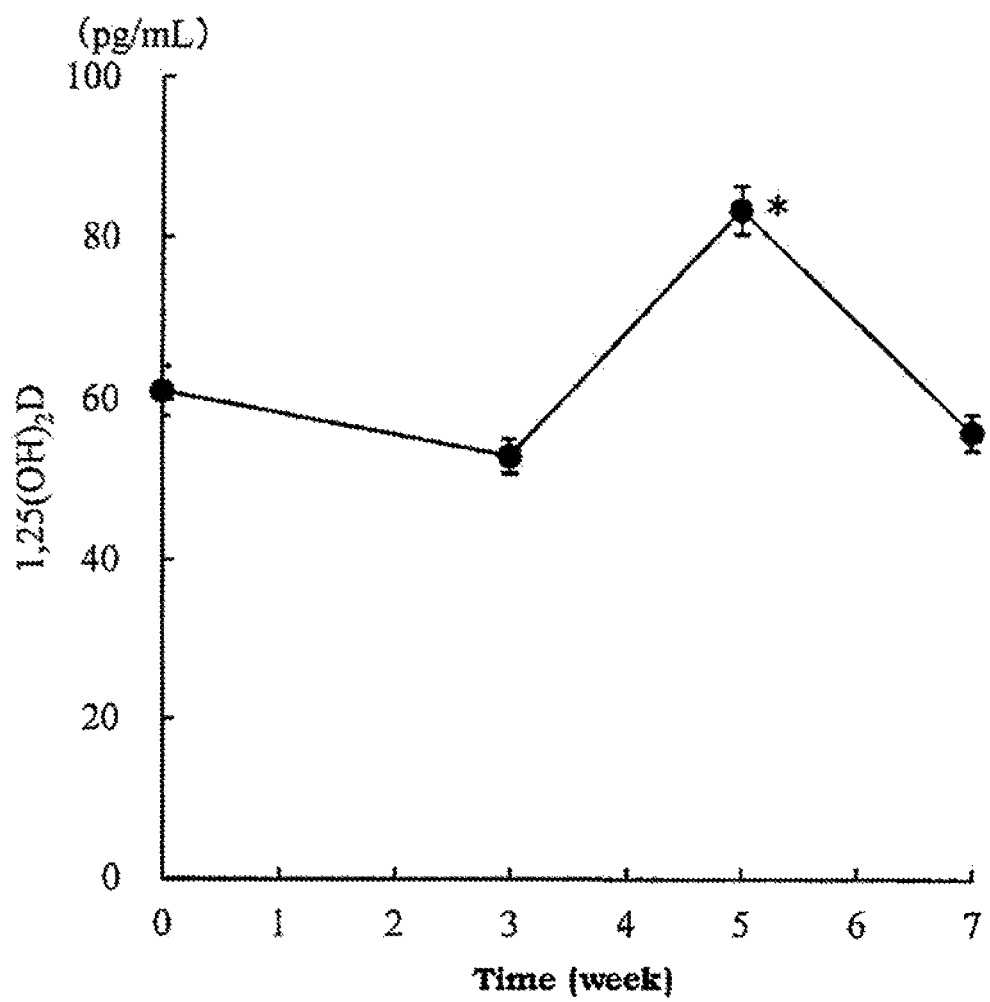
FIG. 8 shows the change in the mean values of the 1,25-$(OH)_2$-D value in the high intake test.

As shown in FIG. 8, 5 weeks after ingestion, a significant increase in 1,25-$(OH)_2$-D level was observed compared with before ingestion. The results suggests that intake of phytic acid increases 1,25-$(OH)_2$-D levels, thereby improves calcium metabolism.

Test Example 5: Effects of Calcium Lactate on the Bitterness and Harsh Taste of Phytic Acid (Test Method)

Sensory tests were performed on two subjects. The test was conducted by tasting the phytic acid beverages of the Comparative Examples and Examples shown in the table below and evaluating them according to the following criteria. The figures in the table show the amounts of dextrin and calcium lactate relative to 100 weight parts of phytic acid. The same amounts of acidulant and sweetener were contained in each of the comparative examples and the examples.

Evaluation Criteria:

On the basis of the bitterness and harsh taste of Comparative Example 1,

Better: 5
Slightly better: 4
Similar: 3
Slightly worse: 2
Worse: 1

Gargling was performed before tasting so that the previous sample did not affect the tasting sample.

|  | Comparative Example 1 | Example 1 | Example 2 | Example 3 | Example 4 | Example 5 |
|---|---|---|---|---|---|---|
| Phytic acid | 100 | 100 | 100 | 100 | 100 | 100 |
| Dextrin | 140 | 140 | 140 | 140 | 140 | 140 |
| Calcium lactate | 0 | 26 | 30 | 40 | 54 | 80 |
| Acidulant | Suitable quantity | Suitable quantity | Suitable quantity | Suitable quantity | Suitable quantity | Suitable quantity |
| Sweetener | Suitable quantity | Suitable quantity | Suitable quantity | Suitable quantity | Suitable quantity | Suitable quantity |
| Water | Suitable quantity | Suitable quantity | Suitable quantity | Suitable quantity | Suitable quantity | Suitable quantity |
| Evaluation | 3 | 4 | 5 | 4 | 3 | 3 |

The invention claimed is:

1. A method for inhibiting intestinal absorption of purine bodies, comprising administering an effective amount of a composition of an inositol phosphate or a salt thereof to a person in need of inhibition of intestinal absorption of purine bodies,
wherein the purine bodies are selected from the group consisting of purine bases, purine nucleosides, purine nucleotides, nucleic acids containing purine nucleotide bases, and mixtures thereof.

2. The method of claim 1,
wherein
said composition further comprises calcium lactate in a weight ratio of inositol phosphate: calcium lactate=1:0.2 to 1:0.5, and
said composition is liquid.

3. A method for inhibiting uric acid level elevation, comprising administering an effective amount of an inositol phosphate or a salt thereof to a person in need of inhibition of uric acid level elevation, wherein a dose of the inositol phosphate or a salt thereof per administration is 10 mg to 15 g as the inositol phosphate.

4. The method of claim 3, wherein administering said inositol phosphate or a salt thereof inhibits absorption of purine bodies selected from the group consisting of purine bases, purine nucleosides, purine nucleotides, nucleic acids containing purine nucleotide bases, and mixtures thereof.

\* \* \* \* \*